Figure 1:
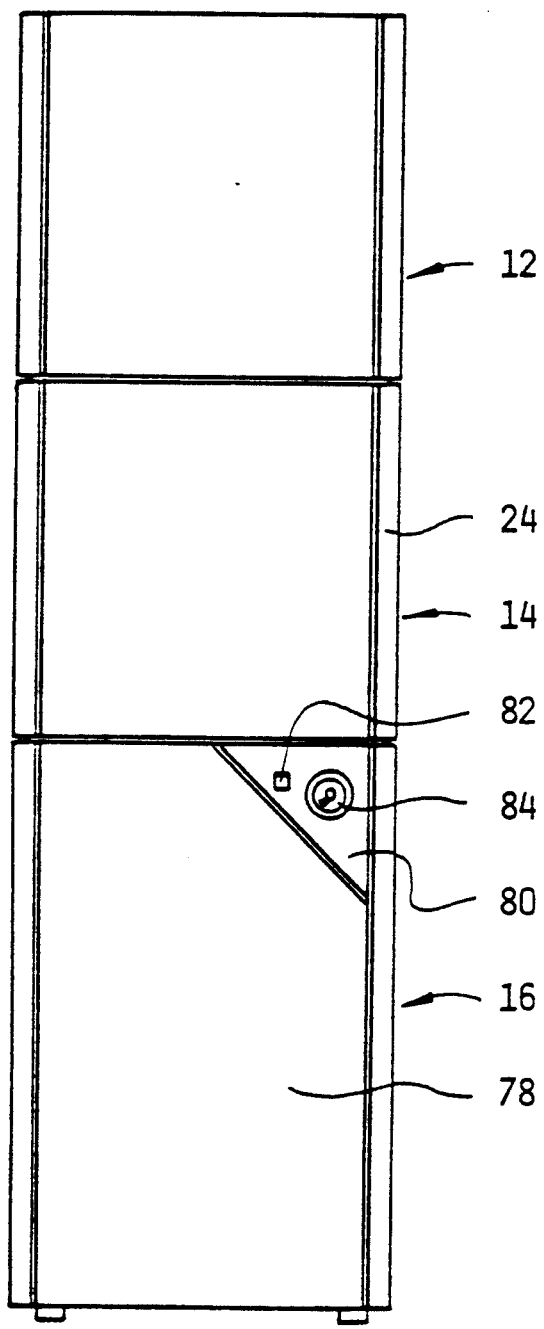

United States Patent [19]

Meyer et al.

[11] Patent Number: 5,222,871
[45] Date of Patent: Jun. 29, 1993

[54] COMPRESSED AIR AND UNDERPRESSURE SUPPLY UNIT

[75] Inventors: Günter Meyer, Bietigheim; Siegfried Nafzger, Steinheim; Reiner Boser, Karlsruhe, all of Fed. Rep. of Germany

[73] Assignee: Durr Dental GmbH & Co KG, Bietigheim-Bissingen, Fed. Rep. of Germany

[21] Appl. No.: 752,571

[22] PCT Filed: Feb. 23, 1990

[86] PCT No.: PCT/EP90/00310

§ 371 Date: Sep. 9, 1991

§ 102(e) Date: Sep. 9, 1991

[87] PCT Pub. No.: WO90/10422

PCT Pub. Date: Sep. 20, 1990

[30] Foreign Application Priority Data

Mar. 9, 1989 [DE] Fed. Rep. of Germany ....... 3907592

[51] Int. Cl.⁵ .................... F04B 23/04; A61G 15/14; A47B 81/00
[52] U.S. Cl. ............... 417/313; 417/423.14; 312/209; 312/265.2; 433/77

[58] Field of Search ............... 417/423.14, 360, 149, 417/426, 313; 312/400, 209, 265.2, 263; 433/77, 92

[56] References Cited

U.S. PATENT DOCUMENTS

| | | | |
|---|---|---|---|
| 3,229,368 | 1/1966 | Tocchini | 312/209 |
| 3,734,122 | 5/1973 | Cousins | 417/313 |
| 4,252,506 | 2/1981 | Hannibal | 417/426 |
| 4,281,883 | 8/1981 | Zacky | 312/263 |
| 4,359,085 | 11/1982 | Mueller | 312/209 |
| 4,441,766 | 4/1984 | Hess | 312/400 |

FOREIGN PATENT DOCUMENTS

226496  6/1987  European Pat. Off. ......... 312/265.1
1151361  3/1955  Fed. Rep. of Germany ...... 312/263

*Primary Examiner*—Richard A. Bertsch
*Assistant Examiner*—Roland McAndrews
*Attorney, Agent, or Firm*—Lowe, Price, LeBlanc & Becker

[57] ABSTRACT

A supply unit for providing compressed air and reduced pressure for dental surgery comprising several superimposed supply components including at least a compressor unit and a suction unit each unit containing a base plate and a cover plate and vertical posts that connect these plates as well as wall panels.

18 Claims, 9 Drawing Sheets

COMPRESSED AIR AND UNDERPRESSURE SUPPLY UNIT

The invention refers to a compressed air and underpressure supply unit for dental surgeries.

Such a supply unit is described in U.S. Pat. No. 3,553,840. In this unit the compressor and the suction unit are mounted in a mobile frame which also carries the compressed air and underpressure consumers, i.e. a saliva remover and a hand-piece providing compressed air. This supply unit represents an emergency supply and disposal unit for a dental surgery which is self-contained, apart from the electrical connection required. No connections to fixed lines in the building are required.

Compressed air and underpressure in dental surgeries which are in constant use are provided partly through lines fixed to the treatment chair and partly through lines laid in the building. Normally a compressor and a suction unit are installed separately in the cellar of the relevant building and connected to the workplace through a compressed air line or an underpressure line. These installations are often fitted by local tradesmen who have no special experience in the relevant field involved. Thus flexible parts of the underpressure line are often laid incorrectly, for example, so that they partly collapse in underpressure during operation and thus only part of the capacity provided by the suction unit is available at the workplace.

This invention is therefore intended to provide a supply unit which can be pre-assembled in the factory so that only a small number of non-critical connections need be made at the point of installation, which can be carried out reliability by tradesmen not specifically trained for such installations.

This task is solved according to the invention by the supply unit described hereinafter.

In the supply unit according to the invention the physical position of the various parts is determined in the factory.

On site only the connections to the fixed supply pipes in the building and the electrical mains network are required. If the supply unit consists of several superimposed components some of the internal connections must be made after the components are superimposed but these are non-critical, straight connections.

As a result, a supply unit according to the invention is no more expensive than a conventional installation because the cost of the frame carrying the compressor and the suction unit, manufactured in series in the factory, is easily compensated for by the savings involved in the reduced installation work on site.

Thus the solution provided by the invention also has the benefit that the installation space required is reduced. This is particularly beneficial in applications where no spacious cellar is available. Also maintenance and repair of the unit according to the invention is easier and faster because the engineer is always dealing with the same unit and does not first have to check the layout of each installation.

In a supply unit according to another embodiment it is also possible to provide an air storage tank and/or a dry air unit within the same small space. Even this supply unit is very easy to install.

The further design of the invention according to another embodiment is advantageous due to the easy manufacture of the frame carrying the unit and consisting of largely identical components.

The further design of the invention according to another embodiment is beneficial due to the low production costs and the attractive appearance of the vertical frame.

A supply unit according to another embodiment has no sharp edges and an attractive appearance.

The further design of the invention according to another embodiment very simply provides sound insulation for the supply unit. This makes it possible to install the attractive supply unit in a room within the dental surgery or laboratory if no cellar or separate room is available.

The further design of the invention according to another embodiment makes it possible to very easily secure the panel components or mounting plates for electronic or fluid trays anywhere on the frame.

The further design of the invention according to another embodiment is of benefit due to the particularly easy installation of the side panel components on the frame.

In a supply unit according to another embodiment it is very easily possible to attach additional mountings for ancillary electrical or fluid units on the inside rear part of the frame.

The further design of the invention according to another embodiment is of benefit due to the particularly easy connection of base plates and vertical frames.

The further design of the invention according to another embodiment serves for a particularly shear-resistant connection between the profiles and the base plates.

In a supply unit according to another embodiment it is possible to secure the fluid lines and electrical cables tidily to the frame away from the heat generating machines.

The further design of the invention according to another embodiment is of benefit due to the clear layout of the internal installations.

A supply unit according to another embodiment can be transported particularly easily since the individual components with the units they carry can easily be carried by two fitters. Storage is also simplified. The combination required for the specific application can easily be produced with components consisting of different units.

The further design of the invention according to another embodiment is of benefit due to the cost-effective production of the supply unit frame. The side walls also increase the stability of the base plates and the cover plates.

The further design of the invention according to another embodiment guarantees in a simple manner the correct alignment of superimposed components in the supply unit.

In a supply unit according to another embodiment there are two parallel tracks at the same height on the underside of a base plate upon which a component can easily be moved on the cover plate of the component below it until the panels of the base plate of the upper component enter the openings in the cover plate of the lower component, thus aligning the components together.

In a supply unit according to another embodiment further fluid lines and electrical cables can be laid from one level to another near the edge of the frame.

In a supply unit according to another embodiment it is very easy to maintain and test the storage tank. This can simply be pivoted out of the interior of the frame, for example, for the pressure safety test which is required periodically.

In a supply unit according to another embodiment it is easily possible to remove the storage tank completely from the frame after it has been pivoted out.

In the supply unit according to the invention there are aligned openings in the various base plates and cover plates which serve not only for laying the fluid lines but also as a ventilation duct once the panels on the frame have been closed. If the top of the frame is also closed by a cover plate, the heat generated by the various units can very easily be dispersed with the aid of this ventilation duct, according to another embodiment.

The further design of the invention according to another embodiment provides operation of the ventilation fan under temperature control.

The further design of the invention according to another embodiment is of benefit concerning vibration-free and therefore low noise operation of the supply unit.

The following section describes the invention in more detail with the aid of the design examples and reference to the drawing. The drawing shows:

FIG. 1: Top view of the front panel of a compressed air and underpressure supply cabinet for a dental surgery, consisting of three superimposed components.

Figure 2:
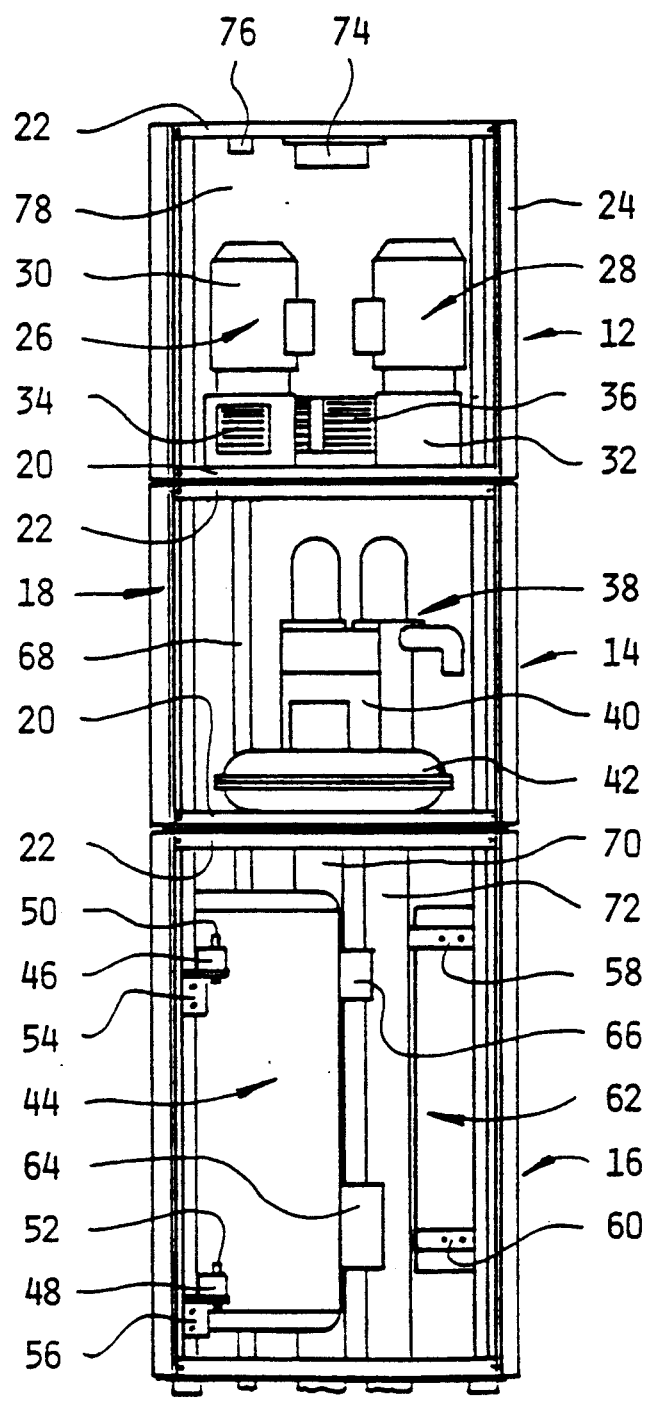

FIG. 2: Top view of the front panel of the supply cabinet according to FIG. 1 after removing the front panels.

Figure 3:
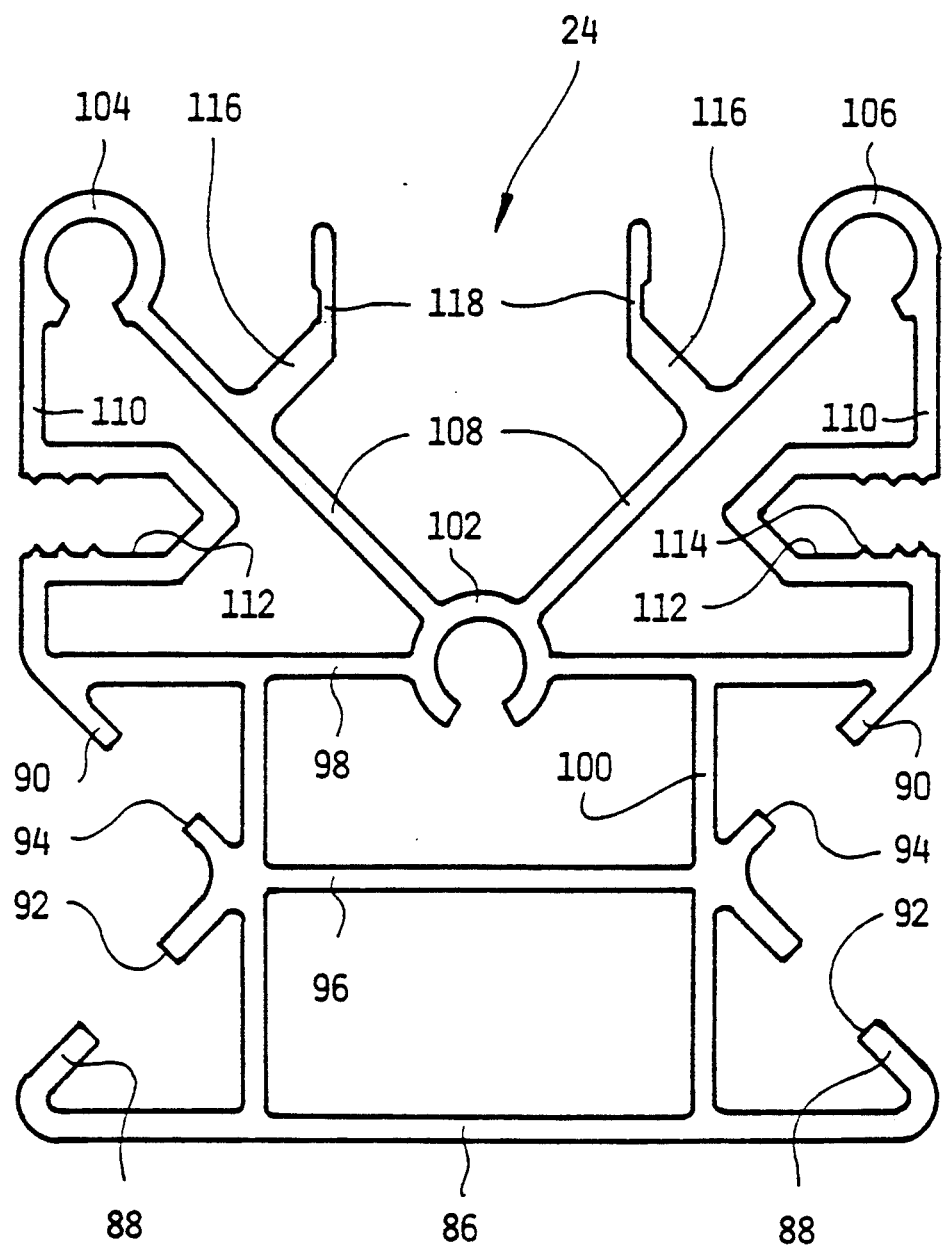

FIG. 3: Enlarged top view of a profile used as a vertical frame in the cabinet components of the supply cabinet according to FIGS. 1 and 2.

Figure 4:
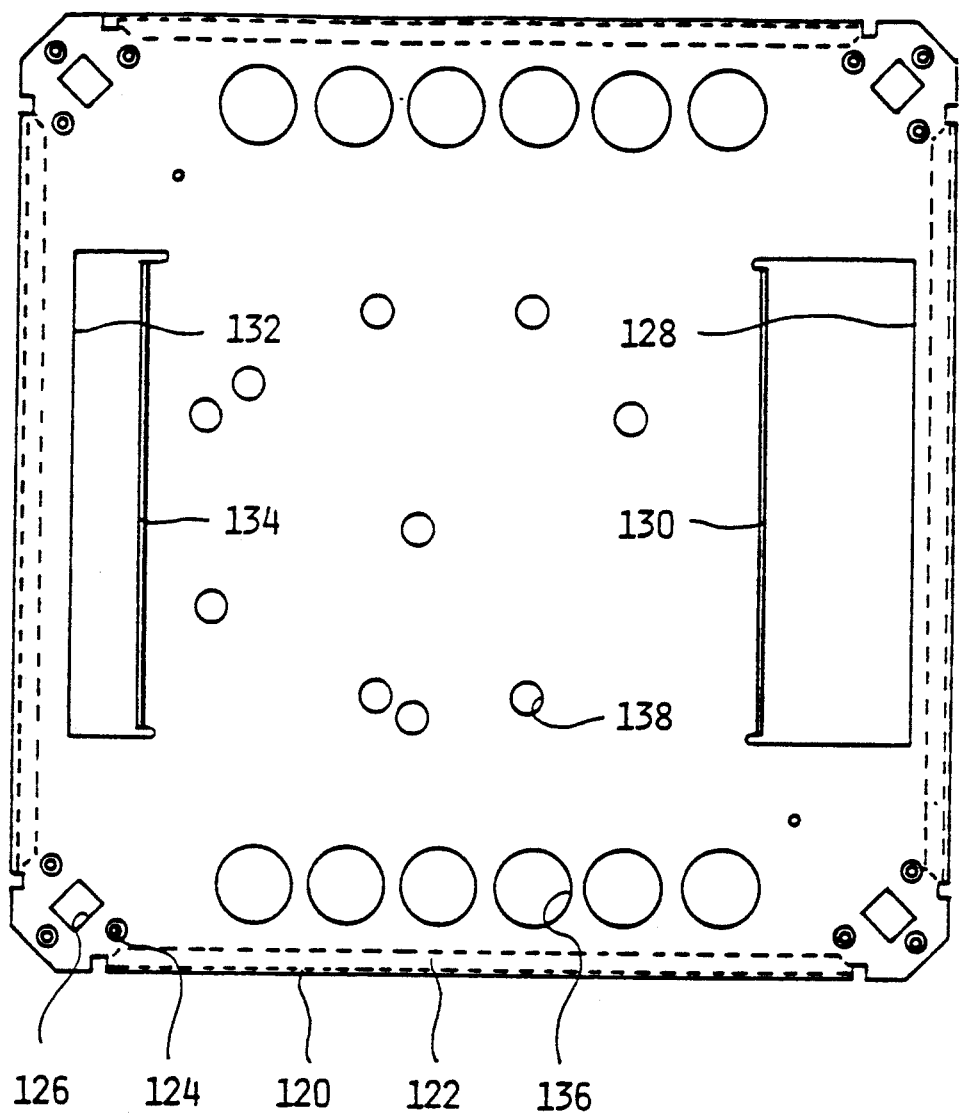

FIG. 4: View of the underside of a base plate for the cabinet components according to FIGS. 1 and 2 in a scale larger than in FIGS. 1 and 2 but smaller than in FIG. 3.

Figure 5:
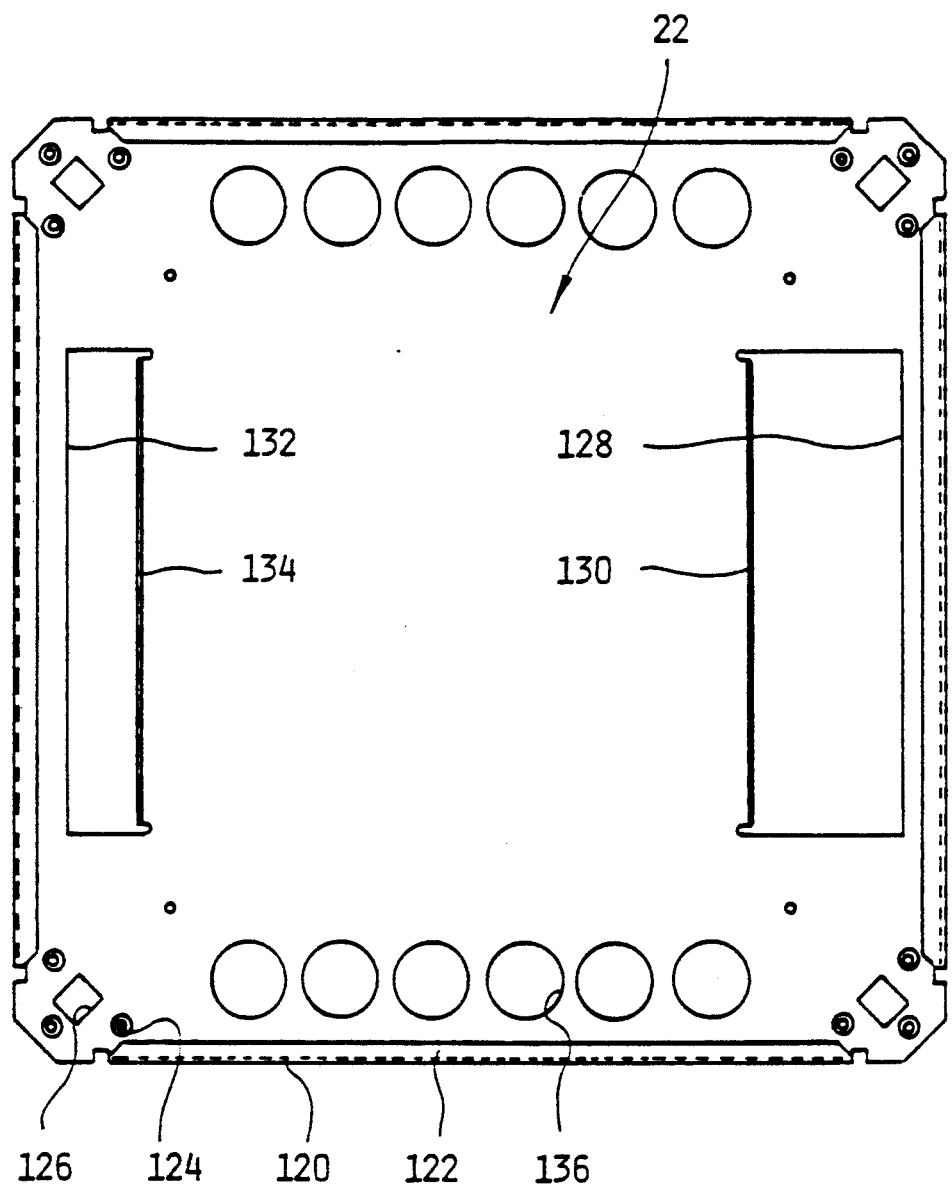

FIG. 5: View of the underside of a cover plate of a cabinet component matching the base plate according to FIG. 4.

Figure 6:
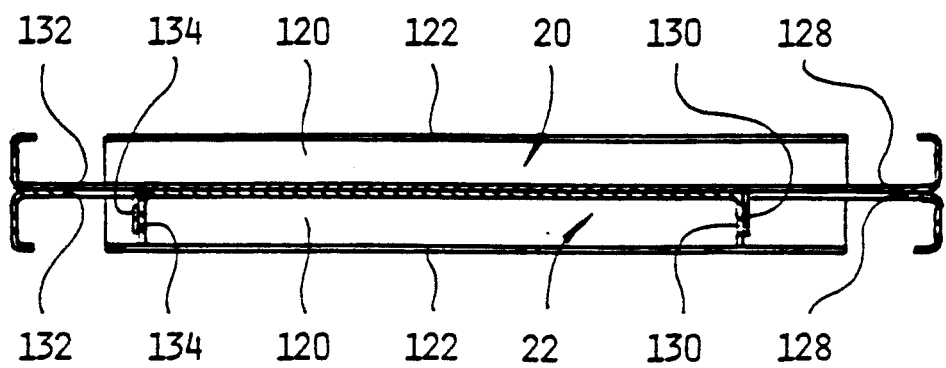

FIG. 6: Longitudinal section through the base plate according to FIG. 4 and the cover plate below this according to FIG. 5 of a lower section of the cabinet along the line VI—VI of FIG. 4 or 5 respectively.

Figure 7:
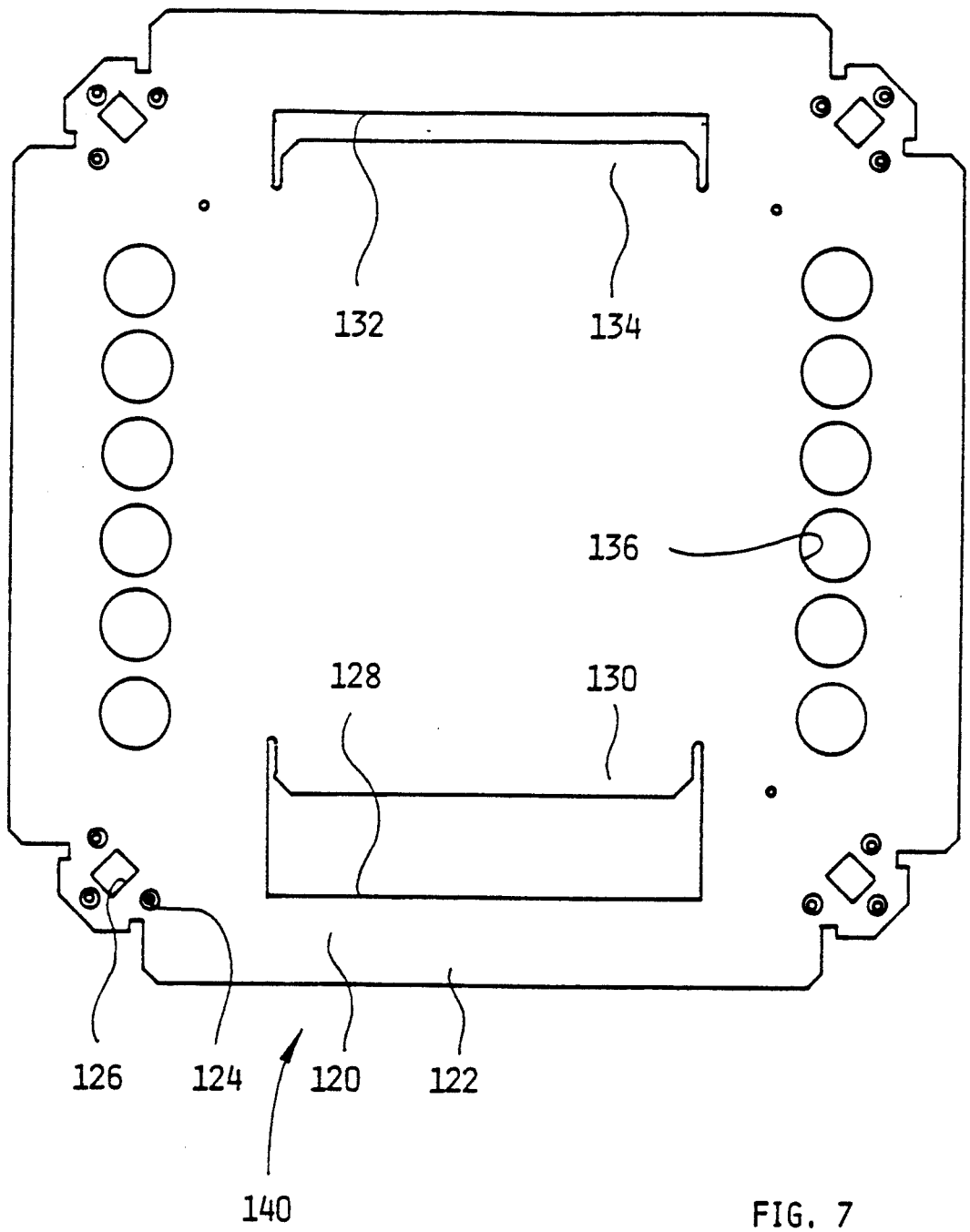

FIG. 7: View of a punched metal part which can be used to produce both the base plate according to FIG. 4 and the cover plate according to FIG. 5.

Figure 8:
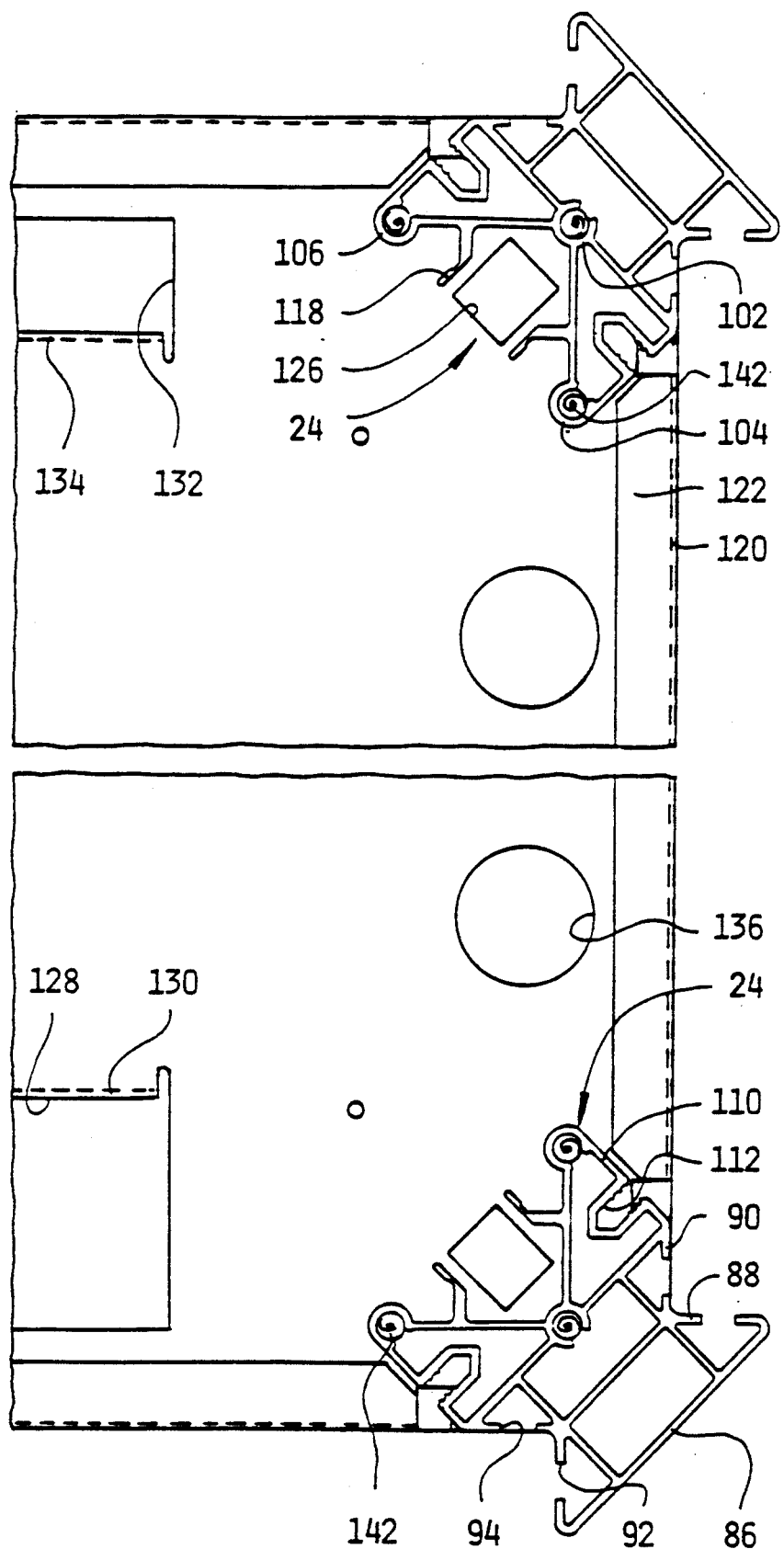

FIG. 8: View of two corners of the frame of a cabinet component after removal of its cover plate.

Figure 9:
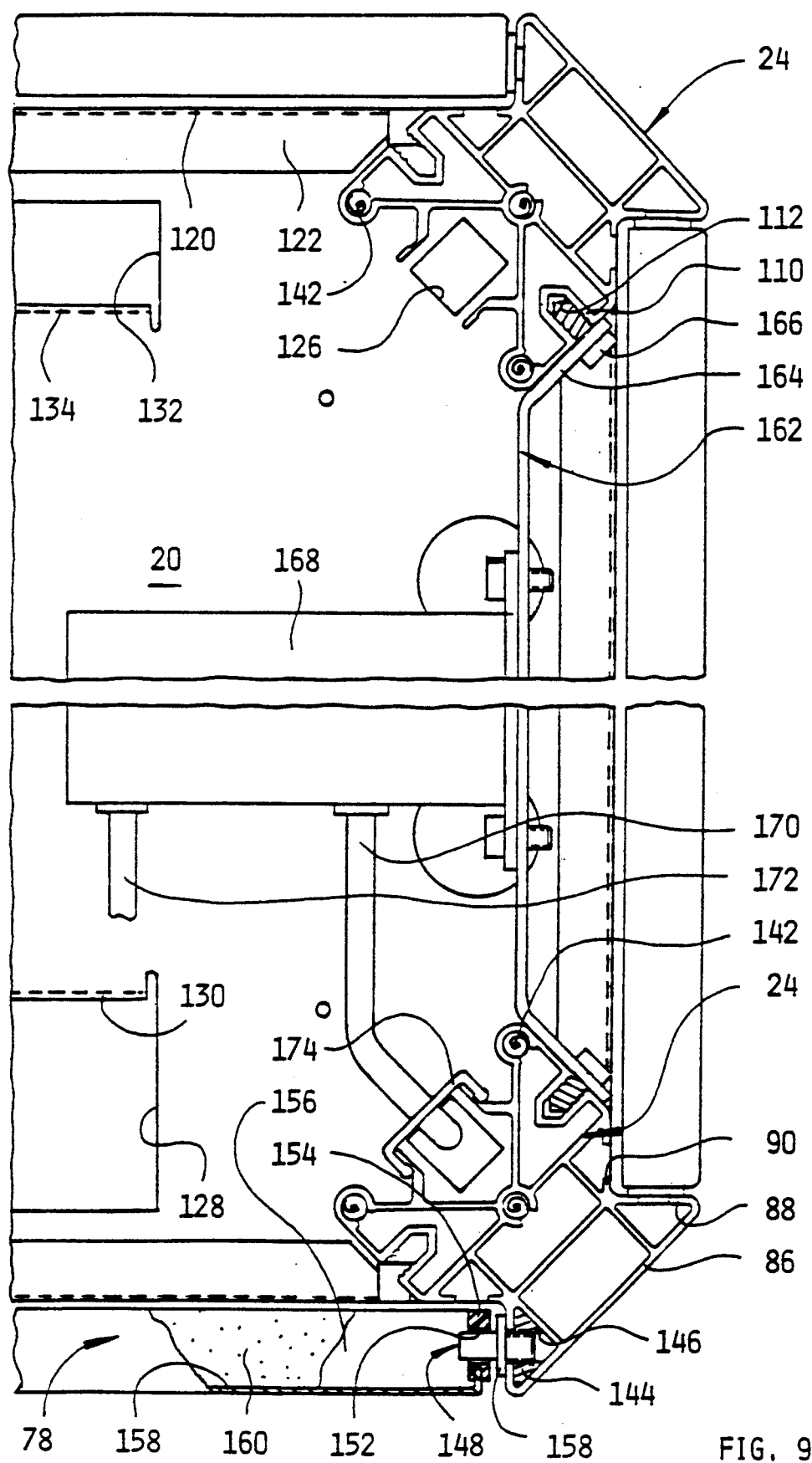

FIG. 9: Similar view as FIG. 8, whereby the side panels are fitted in the frame and a control unit is also mounted on the frame, and FIG. 10: Similar view to FIG. 8 but depicting different versions of the installation.

FIGS. 1 and 2 show a supply unit in the form of a cabinet for dental surgeries consisting of three superimposed supply units (12, 14 and 16). Each of the supply units has a frame designated in total as (18) consisting of a base plate (20), a cover plate (22) and four vertical profiles (24) connecting these plates. The design and connection of the base plates, cover plates and profiles are described in more detail below.

The base plate (20) of the uppermost supply unit (16) carries two piston compressors (26, 28) each of which has an electric motor (30) and two cylinders (34, 36) mounted in a 90° V-shape configuration on a crank casing (32). As shown in the drawing, the motor shafts are vertical and the two piston compressors are mounted on the highest base plate (20) so that their cylinders (34, 36) are symmetrical to the centre axis of the supply unit (16).

The middle supply unit (14) has on its base plate (20) a suction unit (38) which possesses an electric motor (40) and a fan (42) which is flange-mounted to the motor. The shaft of the electric motor (40) is again vertical.

In the lower supply unit (16) there is a compressed air storage tank (44) onto which hinges (46, 48) are welded and mounted on hinged bolts (50, 52). The latter are fitted in angle sections (54, 56) which are bolted to the lefthand front profile (24).

A cylindrical dry air unit (62) is held by support rings (58, 60) bolted to the righthand rear profile (24) of the supply unit (12). The dry air unit contains a drying agent which can be regenerated, such as silica gel, for example, and is connected through lines not shown in FIG. 2 to a control unit (64) mounted on the storage tank (44).

The control unit (64) operates generally so that it normally feeds the compressed air to the storage tank (44) over the drying agent. However, if the treated air has a moisture content above a given value, the control unit pressurises the dry air unit (62) in the opposite direction with air released from the storage tank (44) and the air containing the moisture is released from the dry air unit (62) into the atmosphere.

A pressure sensor (66) is also shown on the storage tank (44) which controls operation of the piston compressors (26, 28).

As shown in FIG. 2, a compressed air line (68) runs vertically from the piston compressors (26, 28) through the uppermost base plate (20), through the cover plates and the base plates of the lower supply units (14, 16) and exits from the supply cabinet at the base, where it is connected to a fixed compressed air line in the building.

A vacuum line (70) and a vent line (72) stretch similarly from the centre supply unit (14) to the floor of the room in which the supply cabinet is installed. The vacuum line (70) is then connected to a vacuum line in the building and the vent line (72) is connected to a vent line leading out over the roof of the building.

The openings in the base plates and cover plates to which the various flow lines (and the electrical cables not shown in FIG. 2 but also grouped at the bottom) run also form a ventilation duct to which the heat generated by the suction unit (38) can rise to the uppermost supply unit (16). The cover plate (22) carries a fan (74) controlled by an adjacent temperature sensor (76). In this way cooling air is drawn by the fan (74) through the base plate of the lowest supply unit (16) and through the supply units (14 and 12).

As shown in FIGS. 1 and 2, the frames (18) of the supply units (12, 14 and 16) are enclosed smoothly on all sides by rectangular panels (78) to provide a cabinet of an attractive appearance together with the visible part of the profiles (24) at an angle of 45° to the panels (78).

The front panel (78) of the lowest supply component (16) is angled at its top righthand corner and a triangular panel (80) is permanently mounted at that point on the frame (18) of this supply component to carry a main switch (82) and a pressure meter (84).

In comparison to FIG. 1, FIG. 3 shows on a much enlarged scale a front view of a profile (24). This profile has a front visible panel (68) with side topes (88) recessed at an angle of 45°. At the rear ends there are rear stop panels (90) which serve as a support for the panels (78).

The stops (88, 90) have slots (92, 94) in the centre for mounting fastening components.

The connection points of the stops (88, 90) are connected by a stiffener (96) parallel to the visible panel (86) and the free ends of the rear stops (90) are connected by a stiffener (98). Further stiffeners (100) which are vertical to the visible panel (86) and the stiffener (98) stretch through the connection points of the stops (88, 90). This produces behind the slots (92, 94) channels of a triangular section in which nuts for securing bolts or similar can be fitted.

Near the centre of the stiffener (98) there is a first screw channel (102) which reaches over an angle of approximately 300°. Further screw channels (104, 106) which also reach over approximately 300° are provided at the ends of two diagonal stiffeners (108) at an angle of +45° and -45° respectively to the stiffener panel (98). Their free ends are connected to the free ends of the stops (90) through further stiffeners (110) vertical to the stiffener (98). These each have a longitudinal moulded groove (112) with small longitudinal ribs (114) which serve for fitting the securing screws.

At the rear of the stiffeners (108) there are cable duct panels (116) which have an end section (118) which is in turn folded back through 45°, i.e. vertical to the level of the stiffener (98). This end section (118) is formed as a bead and a channel cover plate can be fitted onto it.

The profile shown in FIG. 3 is in practice produced by cutting from an aluminium extrusion. Such aluminium extrusions can be produced cost-effectively. Due to the different stiffeners the profile shown in FIG. 3 provides high stiffness for low weight. Without mechanical finishing or with little mechanical reworking (brushing or similar) it provides an attractive visible surface, forms the side and rear stop surfaces for the panels, allows easy assembly of the base plates, cover plates and profiles to form a strong frame, produces a cable duct and also offers facilities for mounting electronic units, fluid units or other ancillary items of equipment which should not be mounted on a base plate or a cover plate, whether for reasons of temperature, protection against vibration or easy access.

As shown in FIG. 4, the base plate (24) have low side walls (120) turned upwards which in turn have a return leg (122) parallel to the base plate. The side panels (120) do not reach into a corner zone where the base plates (20) are bolted to the vertical profiles (24). For this purpose three recessed holes (124) are provided in this corner zone in the same layout as the screw channels (102-106) in the profiles (24).

Inside the triangle produced by the holes (124) there is a rectangular hole (126) which, when the profile is bolted on, is aligned with the adjacent cable channel through the panels (116).

The base plate (20) also has a rectangular opening (128) shown at the right in FIG. 4 whose long edge is very close to the side panel (120) at the right in FIG. 4. At the lefthand edge of the opening (128) a tongue of material (130) is bent downwards.

Similar to the side panel (120) shown at the left in FIG. 4 there is also a slightly narrower rectangular opening (132) whose inside edge also has a tongue of material (134) which is bent downwards. Both tongues of material protrude an equal distance over the underside of the base plate (24) and form tracks on which the base plate can be moved on a lower cover plate.

Along the upper and lower side wall of the base plate (20) there is a number of circular holes (136) which can serve to carry smaller tubes and cables, whilst the opening (128) serves for carrying the compressed air line (68) and the large diameter vacuum line (70) and vent line (72). The opening (132) can also be used for pulling smaller tubes and cables through.

If the openings (128, 132 and 135) are empty or only partly occupied with tubes or cables in a specific installation, they act as openings for cooling air from one supply unit to the next higher unit. As, for example, is shown clearly in FIG. 4, this therefore allows currents of cooling air on all sides of the base plates and cover plates, thus guaranteeing all-round cooling of the units mounted on the base plates. The fan (74) already mentioned sets the cooling air in motion.

Various other small openings (138) in the main part of the base plate serve as mounting points for the piston compressors (26, 28), the vacuum unit (38) or other equipment mounted on such a base plate.

As FIG. 5 shows, the cover plate (22) is of very similar geometry to a base plate (comparable parts of the plates have the same reference) and only the material tongues (130, 134) on the same side are bent like the side panels (120). Furthermore, the material tongues (130, 134) on a cover plate (22) are spaced at slightly smaller intervals than those on a base plate, so that the tongues on a base plate can grip the tongues on a cover plate with some slight play, as shown in FIG. 6.

It is therefore possible to produce base plates and cover plates from the same punched section (140) as shown in FIG. 7. If this section is to be used for base plates, only the additional assembly openings (138) are to be provided. If this is not a problem for a cover plate, exactly the same cut-out can be used for cover plates and base plates. The side panels (120) are then formed with this section and the only difference between the cover plates and the base plates is that on a cover plate the material tongues (130, 134) are bent to the same side as the side panels (120) and on a fold line which lies approximately one thickness of the material further inward than on the base plates where the material tongues (130, 134) are bent towards the side away from the side panels (120).

FIG. 8 shows two corner connections of a frame (18) at a base plate (20).

Self-tapping countersunk metal screws (142) are fitted in the screw channels (102-106) and their heads reach the underside of the base plate (20) and disappear in the countersunk holes (124).

FIG. 8 clearly shows the configuration of the profiles (24) at the corners of the base plate (20) without the side panels (120). One can also clearly see the alignment of the openings (126) in the cable duct produced by the cable duct panels (116, 118).

The lower section of FIG. 9 shows details of the mounting of the outer panels (78) on the profiles (24).

A strip (144) with tapped holes (148) is inserted into the triangular channel behind the slot (92). Two holding lugs (148) are screwed into the tapped holes (146) spaced vertically and a flanged section (150) is supported on the outside of the stop panel (88). The holding lugs (148) fit with slight play in a bayonet slot (152) which has open end not shown in FIG. 9 so that the outer panel (78) can be lifted and removed by pulling it forwards from the frame (18). As shown, the bayonet slot (152) is provided in a plastic component (154) which is fitted in a side panel (156) of the flat shell (158)

of the panel (78). Inside the shell (158) there is a mat of sound installation (160).

A mounting plate (162) is fitted at the righthand side panel of the supply unit shown in FIG. 9. This has ends which are bent through 45° to the level of the panel which lie in front of the stiffeners (110). Self-tapping screws (166) are fitted in the grooves (112) of the stiffener panels (110). In this way the mounting plate (162) is easily accessible directly adjacent to the side panel of the supply unit.

In the design example considered here the mounting plate (162) carries an electrical control unit (168) supplied with power through a cable (170) fed through the cable channel closed by the front profile (124) and leading down to the in-house installation, and also supplied with a load, for example the electric motors (30) or the electric motor (40), through a cable (172) in the supply component. It is understood that in analogy also fluid or purely mechanical units can be mounted on the frame (18) to be easily accessible.

FIG. 9 also shows a cover strip (174) made of a flexible plastic material on the cable duct of the front profile (24).

Figure 10:
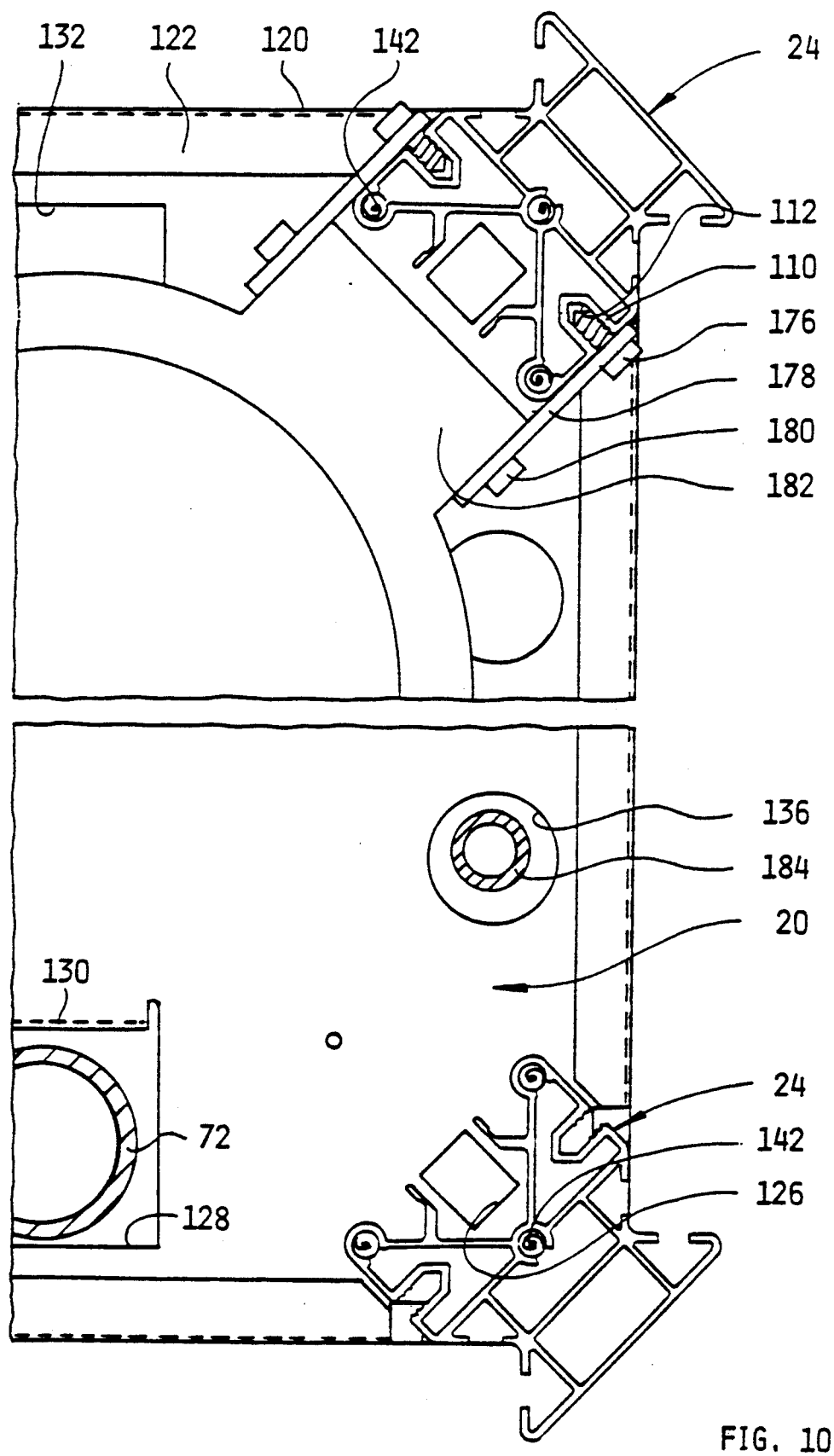

FIG. 10 shows a further possibility for fitting ancillary equipment to the upper profile (24):

Two mounting plates (78) are fitted to the side stiffener panels (110) through pairs of self-tapping screws (176) fitted in the grooves (112). At the free ends of the mounting plates (178) a stop (182) for the upper support ring (58) to which the dry air unit (62) is attached is fixed by means of threaded bolts (180). A similar fastening is provided for the lower support ring (60).

It is clear that such a fastening can easily be fitted at any height on one of the profiles (24) without this having to be machined in any way.

If the mounting is to carry a light weight only, just a single mounting plate can be used.

The large diameter ventilation line (72) is visible in the opening (128) shown in the lower section of FIG. 10. A tube (136) which can, for example, supply cooling water to the dry air unit (62) is also shown in one of the openings (136).

The supply units (12, 14 and 16) are fitted with their equipment in the factory. Also all pressure lines and electrical cables are fitted in the factory with the exception of the short vertical connection leads interconnecting the supply units or connecting them to the in-house installation.

Thus at the point of installation only the supply units (12, 14 and 16) need be positioned accordingly and the vertical connections provided between the components and the in-house installation.

In a modification of the design example described above, the compressed air line (68), the vacuum line (70) and the ventilation line (72) as well as the electrical connection cables can also be fed upwards through the cover plate (22) of the supply unit (16) to the appropriate fixed connection points in the cabinet.

For applications in which sound insulation and/or an attractive appearance of the supply unit is less important it is also possible to leave the panels (78) off the cabinet. The supply unit modified in this way is still characterised by a clear, clean and simple layout.

In a further version of the invention the profiles (24) can run continuously from the bottom to the top for low power supply units and the therefore lighter vacuum unit (38) and a single low power piston compressor (26) can be installed on base plates which are supported on the continuous profiles (24), for example by using brackets which are fitted at the relevant height to the profiles (24) through self-cutting screws in the grooves (112).

We claim:

1. A compressed air and reduced pressure supply unit for dental working places comprising
   (a) a compressor unit (26, 28),
   (b) a suction unit (38);
   (c) a frame (18) upon which said compressor and suction units are mounted, said frame (18) comprising
      (1) a first base plate which carries said compressor unit (26, 28),
      (2) a second base plate spaced away from said first base plate and which carries said suction unit (38),
      (3) a plurality of wall panels (78) disposed at right angles to said base plates,
      (4) vertical posts connecting said spaced apart first and second base plates, each said vertical post comprising an extruded metal profile that includes
         (i) a visible exterior wall (86),
         (ii) first abutment walls (88) extending at an angle of 45° with respect to said visible exterior wall (86) and at an angle of 90° with respect to each other, which abutment walls (88) cooperate with the vertical side edges of said wall panels (78), and
         (iii) second abutment walls (94) that are disposed at an angle of 90° with respect to said first abutment walls (88) and which cooperate with an interior surface of said wall panels (78).

2. A supply unit according to claim 1, wherein that the wall panels comprise trough-shaped shell members and have insulation mats contained therein.

3. A supply unit according to claim 1 wherein said metal profiles have stiffening webs extending from free edges of the second abutment walls in rearward direction being perpendicular to the visible front wall, the stiffening webs being formed with longitudinal channels for fasteners.

4. A supply unit according to claim 1 wherein a storage tank is mounted on one of the vertical metal profiles through vertical hinges for movement between an operating position, wherein the storage tank is located within the contour of the frame, and a service position, wherein the storage tank projects from the frame.

5. A supply unit according to claim 1 wherein the base plates are identical in shape.

6. A supply unit according to claim 1 wherein the said abutment walls are formed with slots receiving fasteners connecting wall panels to the vertical posts.

7. A supply unit according to claim 6 wherein the wall panels comprise bayonet slots cooperating with lugs of the fasteners mounted in the slots of the abutment walls.

8. A supply unit according to claim 1 wherein said metal profiles are formed with at least one screw channel and in that ends of the vertical posts are connected to an associated base plate by means of screws engaging in adjacent ends of the screw channels.

9. A supply unit according to claim 8 wherein the metal profiles are formed with three screw channels, the connection lines of which form an isosceles right triangle.

10. A supply unit according to claim 1 wherein the rear of each metal profile is formed with duct webs forming a cable duct and the base plates have openings lying between these duct webs.

11. A supply unit according to claim 10, wherein free ends of the duct webs are closed by a removable cover.

12. A supply unit according to claim 1 wherein frame subunits are formed by a lower base plate and a cover base plate which are connected through vertical posts and the frame is formed by a stack of such frame subunits.

13. A supply unit according to claim 12 wherein a plurality of circular holes are arranged along an edge of the base plates and the cover plates.

14. A supply unit according to claim 12 wherein the uppermost cover plate carries a fan.

15. A supply unit according to claim 14 wherein the fan is controlled by a temperature sensor suspended below the uppermost cover plate.

16. A supply unit according to claim 12 wherein the base plates and cover plates are sheet metal parts formed with low side walls, the corner portions of the base plates and cover plates having no such side walls.

17. A supply unit according to claim 16 wherein rectangular tongues are formed integral to one of the longitudinal edges of the openings of the base plates and the cover plates are bent out of the plane of the respective plate in opposite direction and the tongues of a base plate and of a cover plate are offset approximately by the thickness of the material so that one of the tongues overlies the other tongue when the frame subunits are stacked one onto the other.

18. A supply unit according to claim 17 wherein the base plates and the cover plates have second openings opposite to those openings through which the fluid lines and electrical cables pass, the tongues belonging to the fluid line and cable receiving openings and the second openings being of the same height.

* * * * *